(12) United States Patent
Knapton et al.

(10) Patent No.: US 9,550,799 B2
(45) Date of Patent: Jan. 24, 2017

(54) PREPARATION OF PHOSPHORUS-CONTAINING ANTIWEAR COMPOUNDS FOR USE IN LUBRICANT COMPOSITIONS

(75) Inventors: Daniel J. Knapton, Willowick, OH (US); Troy A. Conant, Manvel, TX (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 13/819,457

(22) PCT Filed: Aug. 23, 2011

(86) PCT No.: PCT/US2011/048757
§ 371 (c)(1),
(2), (4) Date: May 30, 2013

(87) PCT Pub. No.: WO2012/030581
PCT Pub. Date: Mar. 8, 2012

(65) Prior Publication Data
US 2013/0252864 A1   Sep. 26, 2013

Related U.S. Application Data

(60) Provisional application No. 61/378,430, filed on Aug. 31, 2010.

(51) Int. Cl.
| | | |
|---|---|---|
| C10M 141/10 | (2006.01) | |
| C10M 137/10 | (2006.01) | |
| C10L 1/26 | (2006.01) | |
| C07F 9/09 | (2006.01) | |
| C10M 137/08 | (2006.01) | |

(52) U.S. Cl.
CPC ............... *C07F 9/09* (2013.01); *C07F 9/093* (2013.01); *C10M 137/08* (2013.01); *C10M 2223/043* (2013.01); *C10N 2230/06* (2013.01); *C10N 2270/00* (2013.01)

(58) Field of Classification Search
CPC ........................... C10M 137/02; C10M 137/04
USPC ......................................... 508/421, 423, 425
See application file for complete search history.

(56) References Cited

U.S. PATENT DOCUMENTS

| | | |
|---|---|---|
| 2,411,671 A | 11/1946 | Smith et al. |
| 3,197,405 A | 7/1965 | LeSuer |
| 2008/0182770 A1* | 7/2008 | Ramsey ........................ 508/423 |

FOREIGN PATENT DOCUMENTS

| | | |
|---|---|---|
| WO | 02/102945 | 12/2002 |
| WO | 03/076557 | 9/2003 |
| WO | 2008/094759 | 8/2008 |

OTHER PUBLICATIONS

Written Opinion from corresponding International Application No. PCT/US2011/048757 dated Jan. 23, 2012.
Corresponding International Publication No. WO 2012/030581 A1 and Search Report published Mar. 8, 2012.

* cited by examiner

*Primary Examiner* — Prem C Singh
*Assistant Examiner* — Francis C Campanell
(74) *Attorney, Agent, or Firm* — David M. Shold, Esq.; Teresan W. Gilbert, Esq.

(57) ABSTRACT

A process is provided for preparing a salt of a hydroxy-substituted ester of phosphoric acid, comprising: (a) reacting a phosphate diester with an alkylene oxide, (b) reacting the product mixture of step (a) with a phosphating agent; and (c) reacting the product mixture of step (b) with an amine; wherein the phosphate diester is reacted with the alkylene oxide of step (a) in the substantial absence of a phosphate monoester. The product is useful as an antiwear agent.

13 Claims, No Drawings

PREPARATION OF PHOSPHORUS-CONTAINING ANTIWEAR COMPOUNDS FOR USE IN LUBRICANT COMPOSITIONS

BACKGROUND OF THE INVENTION

The disclosed technology relates to an antiwear agent and lubricating compositions thereof, and an improved method for preparing the antiwear agent. The invention further provides for a method of lubricating a driveline device or a grease application by employing a lubricating composition containing the antiwear agent. The lubricating compositions are also useful in industrial lubrication and metalworking applications.

Driveline power transmitting devices (such as gears or transmissions, especially axle fluids and manual transmission fluids (MTFs)) and grease applications, present highly challenging technological problems and solutions for satisfying the multiple and often conflicting lubricating requirements, while providing durability and cleanliness.

The development of new antiwear chemistry for such applications as gear oils has been driven by the desire to provide chemistries that meet modern lubricating requirements, provide thermo-oxidative stability and cleanliness, and have non-objectionable odor. Many current phosphorus antiwear or extreme pressure additives contain sulfur. Due to increasing environmental concerns, the presence of sulfur in antiwear or extreme pressure additives is becoming less desirable. In addition, many of the sulfur-containing antiwear or extreme pressure additives evolve volatile sulfur species, resulting in lubricating compositions containing antiwear or extreme pressure additives having an odor, which may also be detrimental to the environment or evolve emissions that may be higher than increasingly tighter health and safety legislation specifies.

One development in recent years to address some of these problems is disclosed in PCT Publication WO 2008/094759, Aug. 7, 2008, which reports a lubricating composition of an oil of lubricating viscosity and a sulfur-free amine salt of either (i) a hydroxyl-substituted diester of phosphoric acid, or (ii) a phosphorylated hydroxy-substituted di- or triester of phosphoric acid. In one embodiment, the salt of a hydroxy-substituted diester of phosphoric acid may be prepared by a process comprising (i) reacting a phosphorylating agent with an alcohol, to form a mono- and/or diphosphate ester; reacting the phosphate ester with an alkylene oxide, to form a hydroxy-substituted diester of phosphoric acid; and salting the hydroxy-substituted diester of phosphoric acid with an amine and/or metal.

There is a continuing desire, however, to improve the process for preparing material such as those described in WO 2008/094759. In particular, a process is desired which minimizes the undesirable oligomerization of propylene oxide and leads to higher conversion to desirable products with shorter reaction time.

The disclosed technology, therefore, solves one or more of the above-identified problems by use of the process as described hereinafter.

SUMMARY OF THE INVENTION

The disclosed technology provides a process for preparing a salt of a hydroxy-substituted ester of phosphoric acid, comprising: (a) reacting a phosphate diester with an alkylene oxide, (b) reacting the product mixture of step (a) with a phosphating agent; and (c) reacting the product mixture of step (b) with an amine; wherein the phosphate diester is reacted with the alkylene oxide of step (a) in the substantial absence of a phosphate monoester. In one embodiment the amount of said phosphate monoester is 0 to 10 percent by weight of the total phosphate mono- and diester present.

The disclosed technology also provides the product prepared by the above-mentioned process, and a lubricant comprising an oil of lubricating viscosity and the product so prepared. The technology also provides a method for lubricating a gear, an axle, or a transmission, comprising supplying thereto such a lubricant.

DETAILED DESCRIPTION OF THE INVENTION

Various preferred features and embodiments will be described below by way of non-limiting illustration.

The disclosed technology provides a process for preparing a salt of a hydroxy-substituted ester of phosphoric acid, comprising: (a) reacting a phosphate diester with an alkylene oxide, (b) reacting a product mixture of step (a) with a phosphating agent; and (c) reacting a product mixture of step (b) with an amine; wherein the phosphate diester is reacted with the alkylene oxide of step (a) in the substantial absence of a phosphate monoester.

The first reactant, employed in step (a), comprises a phosphate diester. This will be a material that may be represented by the formula $(RO)_2P(=O)$—OH, wherein each R is independently a hydrocarbyl group having 1 to 30 carbon atoms, or typically a hydrocarbyl group having 4 to 20 carbon atoms, such as 6 to 18 or 6 to 12 or 6 to 10 or 12 to 18 or 14 to 18 carbon atoms. The hydrocarbyl group may, in certain embodiments, be a hydrocarbon group or an alkyl group. The monohydric alcohol may be linear or branched; it may likewise be saturated or unsaturated. In an example, the R groups are alkyl groups and may comprise 2-ethylhexyl groups.

As used in this specification, the term "hydrocarbyl substituent" or "hydrocarbyl group" is used in its ordinary sense, which is well-known to those skilled in the art. Specifically, it refers to a group having a carbon atom directly attached to the remainder of the molecule (in the case of an alcohol, directly attached to the —OH group of the alcohol) and having predominantly hydrocarbon character. Examples of hydrocarbyl groups include:

hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulfoxy);

hetero substituents, that is, substituents which, while having a predominantly hydrocarbon character, in the context of this invention, contain other than carbon in a ring or chain otherwise composed of carbon atoms and encompass substituents as pyridyl, furyl, thienyl and imidazolyl. Heteroatoms include sulfur, oxygen, and nitrogen. In general, no more than two, or no more than one, non-hydrocarbon substituent will be present for every ten carbon atoms in the hydrocarbyl group; alternatively, there may be no non-hydrocarbon substituents in the hydrocarbyl group.

Suitable phosphate diesters are commercially available. They may be prepared by the reaction of phosphorus halide such as phosphorus chloride, PCl$_3$, with an alcohol, typically a monhydric alcohol, followed by chlorination and hydrolysis. Suitable monohydric alcohols include various isomers of octyl alcohols, such as, notably, 2-ethylhexyl alcohol. Other examples of suitable alcohols include butanol, pentanol, hexanol, heptanol, octanol, nonanol, dodecanol, dodecanol, tridecanol, tetradecanol, pentadecanol, hexadecanol, heptadecanol, octadecanol, octadecenol (oleyl alcohol), nonadecanol, eicosyl-alcohol, and mixtures thereof, such as, for example, the 1-isomer of each such alcohol. Examples of suitable alcohols include, for example, 4-methyl-2-pentanol, 2-ethylhexanol, isooctanol, and mixtures thereof.

Examples of commercially available alcohols that may be used include Oxo Alcohol® 7911, Oxo Alcohol® 7900 and Oxo Alcohol® 1100 of Monsanto; Alphanol® 79 of ICI; Nafol® 1620, Alfol® 610 and Alfol® 810 of Condea (now Sasol); Epal® 610 and Epal® 810 of Afton Corporation; Linevol® 79, Linevol® 911 and Dobanol® 25 L of Shell AG; Lial® 125 of Condea Augusta, Milan; Dehydad® and Lorol® of Henkel KGaA (now Cognis) as well as Linopol® 7-11 and Acropol® 91 of Ugine Kuhlmann.

The phosphate diester employed in the reaction of step (a) will be substantially free from phosphate monoester, i.e., RO—P(=O)(OH)$_2$. Moreover, the reaction of step (a) will be conducted in the substantial absence of a phosphate monoester. This means that phosphate monoester may be totally absent from the reaction mixture, or it may be present only in an amount characteristic of an impurity, or it may be present in an amount sufficiently low that it does not interfere with the advantages of the present technology. Suitable amounts of phosphate monoester may include 0 to 10 percent by weight, or 0 to 8 or 0 to 4, or 0 to 2, or 0 to 1, or 0 to 0.5, or 0.1 to 2, or 0.1 to 0.5 percent by weight, or different combinations of these upper and lower amounts. These amounts are expressed as a percentage of the total amount of phosphate mono- and diester present.

The phosphate diester is reacted with an alkylene oxide. The alkylene oxide may contain, for instance, 1 to 16, or 1 to 10, or 2 to 6, or 2 to 4 carbon atoms. Alkylene oxides include those in which an oxygen atom bridges adjacent carbon atoms, for example, 1,2-alkylene oxides. Examples include ethylene oxide, 1,2-propylene oxide, and, 1,2-butylene oxide. C5 and higher alkylene oxides are also envisioned. The alkylene oxide may thus contain, for instance, 2 to 10 or 2 to 6, or 2 to 4, or 3 carbon atoms. In one embodiment, the alkylene oxide comprises 1,2-propylene oxide. While 1,2 alkylene oxides, that is, epoxides, are the commonest of this type of oxide, 1,3 alkylene oxides, that is, 4-membered cyclic ethers, are also known and may be employed. An example is oxetane, i.e., trimethylene oxide.

The reaction of step (a), that is, the reaction between the phosphate diester and the alkylene oxide, is conducted under conditions suitable to effect reaction of the acidic portion of the phosphate diester with the alkylene oxide to form the ester therefrom, typically by ring opening of the alkylene oxide. This reaction may be conducted at elevated temperatures if desired, for instance, 30 to 70° C. or 40 to 60° C. or 45 to 55° C. for a sufficient period of time to allow the desired degree of completion of the reaction. Suitable times will vary with the temperature employed, as is well known to those skilled in the art. Typical times for reaction may include 0.5 to 4 hours, or 1 to 3 hours, or 1.5 to 2.5 hours, i.e., about 2 hours.

The reaction described hereinabove as step (a) will result in a product mixture that will normally comprise at least some molecules represented by the formula

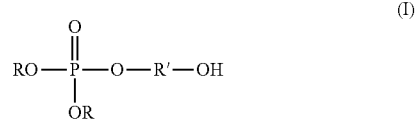

(I)

where each R is independently an alkyl group which will typically be the R groups present on the original phosphate diester reactant. R' originates from the alkylene group of the alkylene oxide. In the case where the alkylene oxide is propylene oxide, at least some molecules present will be represented by the structure

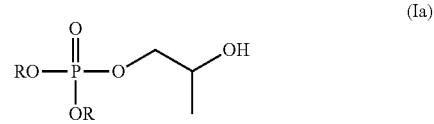

(Ia)

as well as the alternative structure in which the pendant methyl group is attached to the carbon on the left, that is, adjacent to the phosphate group. In certain embodiments of the foregoing structures, each R group will independently be an alkyl group as described in connection with the phosphate diester, above. The reaction mixture may also contain a certain amount of other materials including alkylene oxide dimers or oligomers (initiated by an acidic phosphorus group), materials containing cyclic structures, and various materials with P—O—P linkages, that is, in which the R group in formula (I) can contain phosphorus (which may arise from subsequent reaction with P$_2$O$_5$), as well as materials in which the oxygen atom shown at the right hand side of formula (I) or (Ia) is linked to a phosphorus atom.

The product mixture obtained from step (a) of the reaction, containing some of the material as shown in the structures above, is subsequently reacted with a phosphating agent (alternatively known as a phosphorylating agent). The phosphating agent which may be employed is typically phosphorus pentoxide or a reactive equivalent thereof. Phosphorus pentoxide is usually referred to as P$_2$O$_5$, which is its empirical formula, even though it is believed to consist at least in part of more complex molecules such as P$_4$O$_{10}$. Both such materials have phosphorus in its +5 oxidation state. Other phosphorus materials that may be employed include polyphosphoric acid and phosphorus oxytrihalides (that is, phosphorus oxyhalides) such as phosphorus oxytrichloride.

The intermediate mixture from step (a) may be reacted with the phosphating agent under conditions suitable to provide an acidic phosphate ester by reaction with the free alcoholic OH group of the above structures (I) or (Ia). Suitable conditions for reaction may include heating at 40-60° C. (e.g., 50° C.) and adding phosphorus pentoxide over 2-3 hours, then heating to 70-90° C. (e.g., 80° C.) and holding at that temperature for 1-4 hours, e.g., 3 hours.

The reaction product will be a mixture of individual species, and the particular detailed compositions may depend, to some extent, on the reaction conditions. The reaction mixture, however, will typically contain at least some molecules represented by formula (II)

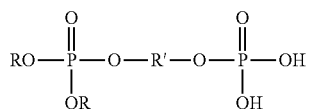

(II)

and isomers thereof, where R and R' are as defined above. In one embodiment the materials may be represented by formula (IIa)

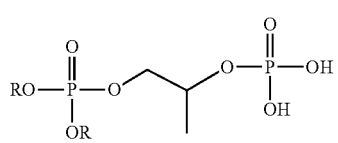

(IIa)

In one embodiment, each R is independently an alkyl group. In certain embodiments, the reaction mixture will contain not only such diacid compounds, but may comprise a mixture thereof with monoacid molecules such as those represented by the formula

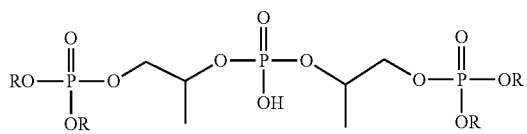

where each R is independently an alkyl group. Thus, typically the product of step (b) comprises a phosphoric ester comprising at least one acid group.

While the above products (II) or (IIa) will normally be the primary and desired products at this stage in the synthesis, other products or intermediates may also be present. These may include

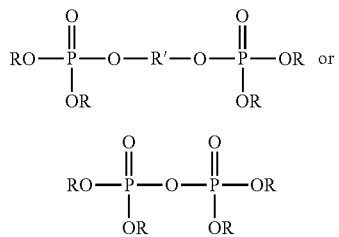

(IIx)

(IIy)

The material (IIy) may be further reactive to provide additional material of structure (II), but the material of (IIx) may not provide additional material of structure (II). Any of these byproducts may be removed from the reaction mixture if desired. Alternatively, they may be allowed to remain in the mixture whereby they may be retained as a minor component of the final product mixture. In general, it is believed that the presence of byproducts such as (IIx) is reduced in materials prepared by the present technology.

The product or intermediate (or mixtures of materials present as the intermediate mixture) prepared from the reaction of the phosphating agent and intermediate from a phosphate diester and an alkylene oxide is further reacted with an amine, to form a mixture of materials that may be characterized as comprising an amine salt or salts. The product includes amine salts of a primary amine, a secondary amine, a tertiary amine, or mixtures thereof. In one embodiment the primary amine includes a tertiary-aliphatic primary amine Other materials, of course, may be present, including some materials having a P—N linkage.

Examples of suitable primary amines include ethylamine, propylamine, butylamine, 2-ethylhexylamine, bis-2-ethylhexylamine, octylamine, and dodecylamine, as well as such fatty amines as n-octylamine, n-decylamine, n-dodecylamine, n-tetradecylamine, n-hexadecylamine, n-octadecylamine and oleyamine. Other useful fatty amines include commercially available fatty amines such as "Armeen®" amines (products available from Akzo Chemicals, Chicago, Ill.), such as Armeen C, Armeen O, Armeen OL, Armeen T, Armeen HT, Armeen S and Armeen SD, wherein the letter designation relates to the fatty group, such as coco, oleyl, tallow, or stearyl groups.

Examples of suitable secondary amines include dimethylamine, diethylamine, dipropylamine, dibutylamine, diamylamine, dihexylamine, diheptylamine, methylethylamine, ethylbutylamine, N-methyl-1-amino-cyclohexane, Armeen® 2C and ethylamylamine. The secondary amines may be cyclic amines such as piperidine, piperazine and morpholine. Examples of tertiary amines include tri-n-butylamine, tri-n-octylamine, tri-decylamine, tri-laurylamine, tri-hexadecylamine, and dimethyloleylamine (Armeen® DMOD).

In one embodiment the amines are in the form of a mixture. Examples of suitable mixtures of amines include (i) an amine with 11 to 14 carbon atoms on tertiary alkyl primary groups (that is, a primary amine with 11 to 14 carbon atoms in a tertiary alkyl group), (ii) an amine with 14 to 18 carbon atoms on tertiary alkyl primary groups (that is, a primary amine with 14 to 18 carbon atoms in a tertiary alkyl group), or (iii) an amine with 18 to 22 carbon atoms on tertiary alkyl primary groups (that is, a primary amine with 18 to 24 carbon atoms in a tertiary alkyl group). Other examples of tertiary alkyl primary amines include tert-butylamine, tert-hexylamine, tert-octylamine (such as 1,1-dimethylhexylamine), tert-decylamine (such as 1,1-dimethyloctylamine), tert-dodecylamine, tert-tetradecylamine, tert-hexadecylamine, tert-octadecylamine, tert-tetracosanylamine, and tert-octacosanylamine. In one embodiment a useful mixture of amines is "Primene® 81R" or "Primene® JMT." Primene® 81R and Primene® JMT (both produced and sold by Rohm & Haas) are mixtures of C11 to C14 tertiary alkyl primary amines and C18 to C22 tertiary alkyl primary amines respectively.

In certain embodiments the amine will comprise at least one secondary amine having 10 to 22 carbon atoms, or 12 to 20, or 14 to 18, or 16 carbon atoms, total. In certain embodiments the secondary amine will contain two alkyl groups, each having 5 to 11 carbon atoms, or 6 to 10, or 7 to 9 carbon atoms. An example is di(ethylhexyl)amine.

In certain embodiments the amine salt will comprise a mixture of materials which will include some molecules represented by the structure of formula (III)

formula (III)

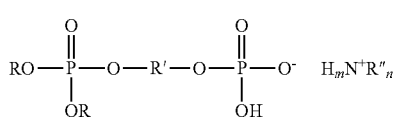

wherein m and n are both positive non-zero integers, provided that the sum of (m+n) is equal to 4. It is contemplated that typically only one of the acidic OH groups of formula (II) will be neutralized by the amine, although under certain condition multiple acidic OH groups might be neutralized.

It is evident that the anionic portion of formula (III), on the left, is a representation of an anion derived from a material of formula (I), (Ia), (II), or (IIa), and each of the foregoing representations and descriptions in connection with those formulas will also be applicable to the anionic portion of formula (III). Likewise, the cationic portion of formula (III), on the right, is a representative of a cation derived from an amine as described above, and R" will represent a hydrocarbyl group from such an amine. In one embodiment, each R" is independently a hydrocarbyl group of 1-22 carbon atoms.

The amine salt which includes, as an example, the material of formula (III), may also contain a portion of one or more metal ions. That is, it may be a mixed amine and metal salt. In certain embodiments at least half of the valence of the anionic portion in the overall product composition will be satisfied by an amine cation, or at least 75% or at least 90%. In one embodiment the salt does not contain a metal ion. The metal ion, if present, may be from a mono- or divalent metal, or mixtures thereof. In one embodiment the metal ion is divalent. In one embodiment the metal of the metal ion includes lithium, sodium, potassium, calcium, magnesium, barium, copper, nickel, tin, or zinc. In one embodiment the metal of the metal ion includes lithium, sodium, calcium, magnesium, or zinc. In one embodiment the metal of the metal ion is zinc.

It is known that some of the materials described above may interact in the final formulation, so that the components of the final formulation may be different from those that are initially added. For instance, metal ions (of, e.g., a detergent) can migrate to other acidic or anionic sites of other molecules, such as the product described above. The products formed thereby, including the products formed upon employing the composition of the present invention in its intended use, may not be susceptible of easy description. Nevertheless, all such modifications and reaction products are included within the scope of the present technology; the present technology encompasses the composition prepared by admixing the components described herein.

The amine salt compositions described above will typically be used in a lubricant composition. One of the components of a lubricant composition is an oil of lubricating viscosity. These include natural and synthetic oils of lubricating viscosity, oils derived from hydrocracking, hydrogenation, or hydro-finishing, and unrefined, refined, and re-refined oils and mixtures thereof.

Natural oils include animal oils, vegetable oils, mineral oils and mixtures thereof. Synthetic oils include hydrocarbon oils, silicon-based oils, and liquid esters of phosphorus-containing acids. Synthetic oils may be produced by Fischer-Tropsch gas-to-liquid synthetic procedure as well as other gas-to-liquid oils. In one embodiment the composition of the present invention is useful when employed in a gas-to-liquid oil. Often Fischer-Tropsch hydrocarbons or waxes may be hydroisomerized. In one embodiment the base oil comprises a polyalphaolefin including a PAO-2, PAO-4, PAO-5, PAO-6, PAO-7, or PAO-8. The polyalphaolefin in one embodiment is prepared from dodecene and in another embodiment from decene. In one embodiment the oil of lubricating viscosity is an ester such as an adipate.

Oils of lubricating viscosity may also be defined as specified in the American Petroleum Institute (API) Base Oil Interchangeability Guidelines. In one embodiment the oil of lubricating viscosity comprises an API Group I, II, III, IV, V, VI base oil, or mixtures thereof, and in another embodiment API Group II, III, IV base oil or mixtures thereof. In another embodiment the oil of lubricating viscosity is a Group III or IV base oil and in another embodiment a Group IV base oil.

The amount of the oil of lubricating viscosity present is typically the balance remaining after subtracting from about 100 wt % the sum of the amount of the compounds of the present technology and other listed components such as friction modifier, conventional phosphorus antiwear and/or extreme pressure agent, organo-sulfide, and other performance additives. In one embodiment the lubricating composition is in the form of a concentrate and/or a fully formulated lubricant. If the phosphorus containing additive and any other performance additives are in the form of a concentrate (which may be combined with additional oil to form, in whole or in part, a finished lubricant), the ratio of the components of the lubricating composition to the oil of lubricating viscosity and/or to diluent oil include the ranges of 1:99 to about 99:1 by weight, or 80:20 to 10:90 by weight.

The lubricant formulation may contain a viscosity modifier (which is sometimes counted as a part of the oil of lubricating viscosity component). Viscosity modifiers (VM) and dispersant viscosity modifiers (DVM) are well known. Examples of VMs and DVMs may include polymethacrylates, polyacrylates, polyolefins, styrene-maleic ester copolymers, and similar polymeric substances including homopolymers, copolymers, and graft copolymers. The DVM may comprise a nitrogen-containing methacrylate polymer, for example, a polymer derived from methyl methacrylate and dimethylaminopropyl amine, e.g., from a monomer derived, in turn, from methyl methacrylate and dimethylaminopropyl amine.

Examples of commercially available VMs, DVMs and their chemical types may include the following: polyisobutylenes (such as Indopol™ from BP Amoco or Parapol™ from ExxonMobil); olefin copolymers (such as Lubrizol™ 7060, 7065, and 7067 from Lubrizol and Lucant™ HC-2000L and HC-600 from Mitsui); hydrogenated styrene-diene copolymers (such as Shellvis™ 40 and 50, from Shell and LZ® 7308, and 7318 from Lubrizol); styrene/maleate copolymers, which are dispersant copolymers (such as LZ® 3702 and 3715 from Lubrizol); polymethacrylates, some of which have dispersant properties (such as those in the Viscoplex™ series from RohMax, the Hitec™ series from Afton, and LZ 7702™, LZ 7727™, LZ7725™ and LZ 7720C™ from Lubrizol); olefin-graft-polymethacrylate polymers (such as Viscoplex™ 2-500 and 2-600 from RohMax); and hydrogenated polyisoprene star polymers (such as Shellvis™ 200 and 260, from Shell). Viscosity modifiers that may be used are described in U.S. Pat. Nos. 5,157,088, 5,256,752 and 5,395,539. The VMs and/or DVMs may be used in the functional fluid at a concentration of up to 20% by weight. Concentrations of 1 to 12%, or 3 to 10% by weight may be used.

The lubricant formulation may contain, in addition the phosphorus salt composition described above, one or more conventional phosphorus antiwear agents and/or extreme pressure agents. Alternatively, the lubricant formulation may be free from such conventional agents. The conventional phosphorus antiwear and/or extreme pressure agent may be present in an amount of 0 wt % to 10 wt %, 0 wt % to 8 wt %, 0 wt % to 6 wt %, 0.05 wt % to 2.5 wt %, 1 wt % to 2 wt %, and 0.05 wt % to 4 wt % of the lubricating composition. Suitable agents include those described in U.S. Pat. No. 3,197,405; see for instance examples 1 to 25 thereof.

The conventional phosphorus antiwear and/or extreme pressure agent may include a non-ionic phosphorus compound, an amine salt of a phosphorus compound other than those disclosed above (such as an amine salt of a mixture of monoalkyl and dialkyl phosphoric acid esters), an ammonium salt of a phosphorus compound other than those disclosed above, a metal dialkyldithiophosphate, a metal dialkylphosphate, or mixtures thereof. In one embodiment the conventional phosphorus antiwear or extreme pressure agent is selected from the group consisting of non-ionic phosphorus compound, a metal dialkyldithiophosphate, a metal dialkylphosphate, and mixtures thereof.

In one embodiment the conventional phosphorus antiwear and/or extreme pressure agent includes a metal dialkyldithiophosphate. The alkyl groups of the dialkyldithiophosphate may be linear or branched and may contain 2 to 20 carbon atoms, provided that the total number of carbons is sufficient to make the metal dialkyldithiophosphate oil soluble. The metal of the metal dialkyldithiophosphate typically includes monovalent or divalent metals. Examples of suitable metals include sodium, potassium, copper, calcium, magnesium, barium, or zinc. In one embodiment the phosphorus-containing acid, salt or ester is a zinc dialkyldithiophosphate. Examples of suitable zinc dialkylphosphates (often referred to as ZDDP, ZDP or ZDTP) include zinc di-(2-methylpropyl)dithiophosphate, zinc di-(amyl)dithiophosphate, zinc di-(1,3-dimethylbutyl)dithiophosphate, zinc di-(heptyl)dithiophosphate, zinc di-(octyl)dithiophosphate, zinc di-(2-ethylhexyl)dithiophosphate, zinc di-(nonyl)dithiophosphate, zinc di-(decyl)dithiophosphate, zinc di-(dodecyl)dithiophosphate, zinc di-(dodecylphenyl)dithiophosphate, zinc di-(heptylphenyl)dithiophosphate, and ZDDPs prepared from mixed alcohols such as methylpropyl and amyl alcohols, 2-ethylhexyl and isopropyl alcohols, or 4-methyl-2-pentyl and isopropyl alcohols; or mixtures thereof.

In one embodiment the conventional phosphorus antiwear and/or extreme pressure agent includes a metal hydrocarbylphosphate or dihydrocarbylphosphate. The hydrocarbyl group of the metal dialkylphosphate includes a straight-chain or a branched alkyl group, a cyclic alkyl group, a straight-chain or a branched alkenyl group, an aryl group, or an arylalkyl group. In one embodiment the hydrocarbyl group of the metal dialkylphosphate is an oil soluble alkyl group. The alkyl group typically includes about 1 to about 40, or about 4 to about 40, or about 4 to about 20, or about 6 to about 16 carbon atoms. Examples of suitable hydrocarbyl or alkyl groups are listed in WO 2008/094759, paragraphs 0069 through 0076.

In one embodiment the metal hydrocarbylphosphate or dihydrocarbylphosphate includes a metal salt of a monoalkyl phosphate, and in another embodiment a metal salt of a di-alkyl phosphate. In one embodiment the metal of the metal hydrocarbylphosphate or dihydrocarbylphosphate is a monovalent metal, in another embodiment the metal is divalent, and in another embodiment the metal is trivalent. The metal of the metal hydrocarbylphosphate or dihydrocarbylphosphate may include aluminum, calcium, magnesium, strontium, chromium, iron, cobalt, nickel, zinc, tin, lead, manganese, silver, or mixtures thereof. In one embodiment the metal is zinc.

In one embodiment the lubricating composition further comprises an organo-sulfide. In one embodiment the organo-sulfide comprises at least one of a polysulfide, thiadiazole compound, or mixtures thereof. In different embodiments, the organo-sulfide is present in a range of 0 wt % to 10 wt %, 0.01 wt % to 10 wt %, 0.1 wt % to 8 wt %, 0.25 wt % to 6 wt %, 2 wt % to 5 wt %, or 3 wt % to 5 wt % of the lubricating composition.

Examples of a thiadiazole include 2,5-dimercapto-1,3,4-thiadiazole, or oligomers thereof, a hydrocarbyl-substituted 2,5-dimercapto-1,3-4-thiadiazole, a hydrocarbylthio-substituted 2,5-dimercapto-1,3-4-thiadiazole, or oligomers thereof. The oligomers of hydrocarbyl-substituted 2,5-dimercapto-1,3-4-thiadiazole typically form by forming a sulfur-sulfur bond between 2,5-dimercapto-1,3-4-thiadiazole units to form oligomers of two or more of said thiadiazole units. Further examples of thiadiazole compounds are found in WO 2008,094759, paragraphs 0088 through 0090.

The organosulfide may alternatively be a polysulfide. In one embodiment at least about 50 wt % of the polysulfide molecules are a mixture of tri- or tetra-sulfides. In other embodiments at least about 55 wt %, or at least about 60 wt % of the polysulfide molecules are a mixture of tri- or tetra-sulfides. The polysulfides include sulfurized organic polysulfides from oils, fatty acids or ester, olefins or polyolefins.

Oils which may be sulfurized include natural or synthetic oils such as mineral oils, lard oil, carboxylate esters derived from aliphatic alcohols and fatty acids or aliphatic carboxylic acids (e.g., myristyl oleate and oleyl oleate), and synthetic unsaturated esters or glycerides.

Fatty acids include those that contain 8 to 30, or 12 to 24 carbon atoms. Examples of fatty acids include oleic, linoleic, linolenic, and tall oil. Sulfurized fatty acid esters prepared from mixed unsaturated fatty acid esters such as are obtained from animal fats and vegetable oils, including tall oil, linseed oil, soybean oil, rapeseed oil, and fish oil.

The polysulfide may also derived from an olefin derived from a wide range of alkenes, typically having one or more double bonds. The olefins in one embodiment contain 3 to 30 carbon atoms. In other embodiments, olefins contain 3 to 16, or 3 to 9 carbon atoms. In one embodiment the sulfurized olefin includes an olefin derived from propylene, isobutylene, pentene, or mixtures thereof. In one embodiment the polysulfide comprises a polyolefin derived from polymerizing, by known techniques, an olefin as described above. In one embodiment the polysulfide includes dibutyl tetrasulfide, sulfurized methyl ester of oleic acid, sulfurized alkylphenol, sulfurized dipentene, sulfurized dicyclopentadiene, sulfurized terpene, and sulfurized Diels-Alder adducts; phosphosulfurized hydrocarbons.

In one embodiment the lubricating composition further comprises a friction modifier. In different embodiments, the friction modifier is present in an amount of 0 wt % to 7 wt %, 0.1 wt % to 6 wt %, 0.25 wt % to 5 wt %, or 0.5 wt % to 5 wt % of the lubricating composition.

The friction modifier includes fatty amines, borated glycerol esters, fatty acid amides, non-borated fatty epoxides, borated fatty epoxides, alkoxylated fatty amines, borated alkoxylated fatty amines, metal salts of fatty acids, fatty imidazolines, metal salts of alkyl salicylates (which may also be referred to as a detergent), metal salts of sulfonates (which may also be referred to as a detergent), condensation products of carboxylic acids or polyalkylene-polyamines, or amides of hydroxyalkyl compounds. In one embodiment the friction modifier includes a fatty acid ester of glycerol. The fatty acids may contain 6 to 24, or 8 to 18 carbon atoms. In one embodiment the friction modifier may comprise the product of isostearic acid with tetraethylenepentamine. A more detailed list of possible friction modifiers is found in WO 2008/094759, paragraphs 0100 through 0113.

The composition of the invention optionally further includes at least one other performance additive. The other performance additives include metal deactivators, detergents, dispersants, antioxidants, corrosion inhibitors, foam inhibitors, demulsifiers, pour point depressants, seal swelling agents, and mixtures thereof. In different embodiments, the total combined amount of the other performance additive compounds is present at 0 wt % to 25 wt %, about 0.1 wt % to 15 wt %, or 0.5 wt % to 10 wt %, of the lubricating composition. Although one or more of the other performance additives may be present, it is common for the other performance additives to be present in different amounts relative to each other.

Antioxidants include molybdenum compounds such as molybdenum dithiocarbamates, sulfurized olefins, hindered phenols, aminic compounds such as alkylated diphenylamines (typically di-nonyl diphenylamine, octyl diphenylamine, or di-octyl diphenylamine).

Detergents include neutral or overbased detergents, Newtonian or non-Newtonian, basic salts of alkali, alkaline earth or transition metals with one or more of a phenate, a sulfurized phenate, a sulfonate, a carboxylic acid, a phosphorus acid, a mono- and/or a di-thiophosphoric acid, a saligenin, an alkylsalicylate, and a salixarate.

Dispersants include N-substituted long chain alkenyl succinimides, as well as Mannich condensation products as well as post-treated versions thereof. Post-treated dispersants include those by reaction with urea, thiourea, dimercaptothiadiazoles, carbon disulfide, aldehydes, ketones, carboxylic acids, hydrocarbon-substituted succinic anhydrides, nitriles, epoxides, boron compounds, and phosphorus compounds. In one embodiment the dispersant includes a borated polyisobutylene succinimide. Typically the number average molecular weight of the polyisobutylene ranges from about 450 to 5000, or 550 to 2500. In different embodiments, the dispersant is present in an amount of 0 wt % to 10 wt %, 0.01 wt % to 10 wt %, or 0.1 wt % to 5 wt % of the lubricating composition.

Corrosion inhibitors include octylamine octanoate, condensation products of dodecenyl succinic acid or anhydride, condensation products of a fatty acid such as oleic acid with a polyamine, or a thiadiazole compound described above. Metal deactivators include derivatives of benzotriazoles (typically tolyltriazole), 1,2,4-triazoles, benzimidazoles, 2-alkyldithiobenzimidazoles or 2-alkyldithiobenzothiazoles.

Foam inhibitors include polysiloxanes as well as copolymers of ethyl acrylate and 2-ethylhexylacrylate and optionally vinyl acetate. Demulsifiers include trialkyl phosphates, polyethylene glycols, polyethylene oxides, polypropylene oxides and (ethylene oxide-propylene oxide) polymers. Pour point depressants include esters of maleic anhydride-styrene, polymethacrylates, polyacrylates, or polyacrylamides. Seal swell agents include Exxon Necton-37™ (FN 1380) and Exxon Mineral Seal Oil (FN 3200).

In one embodiment the lubricating composition described herein may be a grease, and such compositions typically will further comprises a grease thickener. The grease thickener includes materials derived from (i) inorganic powders such as clay, organo-clays, bentonite, fumed silica, calcite, carbon black, pigments, copper phthalocyanine or mixtures thereof, (ii) a carboxylic acid and/or ester (such as a mono- or poly-carboxylic acid and/or ester thereof), (iii) a polyurea or diurea, or (iv) mixtures thereof. A detailed description of specific grease thickeners is found in WO 2008/094759, paragraphs 0135 through 0145. A grease composition may also contain one or more metal deactivators, antioxidants, antiwear agents, rust inhibitors, viscosity modifiers, extreme pressure agents (as described above) or a mixture of two or more thereof.

In one embodiment the present technology provides a method of lubricating a driveline device (such as a gear, axle, or transmission) comprising supplying to the driveline device a lubricating composition disclosed herein. The lubricant may be a grease. The driveline device may comprises at least one of a gear, a gearbox, an axle gear, a traction drive transmission, an automatic transmission or a manual transmission. In one embodiment the driveline device is a manual transmission or a gear, a gearbox, or an axle gear. The automatic transmission may be a continuously variable transmission (CVT), an infinitely variable transmission (IVT), a torroidal transmission, a continuously slipping torque converted clutche (CSTCC), a stepped automatic transmission, or a dual clutch transmission (DCT).

In one embodiment the invention provides for the use of the lubricating composition disclosed herein in gears and transmissions to impart at least one of antiwear performance, extreme pressure performance, acceptable deposit control, acceptable oxidation stability, and reduced odor.

The amount of each chemical component described is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

EXAMPLES

Example 1

300 g of di-(2-ethylhexyl)phosphoric acid (the diester) is heated to 40° C. under a gentle stream of nitrogen with mixing. 51.0 g propylene oxide is added to the acid via a sub-surface tube over a period of 2 hours. The reaction mixture is warmed to 70° C. and held at this temperature for 2 hours, after which it is vacuum stripped at <4 kPa (<30 torr) for 1 hour. The resultant mixture is cooled to 50° C. under a gentle stream of nitrogen with stirring, at which time 35.5 g of phosphorus pentoxide is added over a period of 2 hours. The reaction mixture is warmed to 80° C., held at this temperature for 3 hours, and filtered. The reaction mixture is then re-warmed to 48° C. under a gentle stream of nitrogen with stirring, at which time 109 g of bis-2-ethylhexyl amine is added drop-wise over a period of 2-2.5 hours. The reaction mixture is warmed to 75° C. and held at this temperature for 2.5 hours. The reaction product is used without further purification.

Reference Example 2

300 g of a mixture of di-(2-ethylhexyl) and 2-ethylhexyl phosphoric acid is heated to 40° C. under a gentle stream of nitrogen with mixing. 62.0 g propylene oxide is added to the acid via a sub-surface tube over a period of 2 hours. The reaction mixture is warmed to 70° C. and held at this temperature for 2 hours, upon which it is vacuum stripped at <4 kPa (<30 torr) for 1 hour. The resultant mixture is cooled to 50° C. under a gentle stream of nitrogen with stirring, at which time 39.3 g of phosphorus pentoxide is added over a period of 2 hours. The reaction mixture is warmed to 80° C., held at this temperature for 3 hours, and filtered. The reaction mixture is then re-warmed to 48° C. under a gentle stream of nitrogen with stirring, at which time 138 g of bis-2-ethylhexyl amine is added drop-wise to the reaction mixture over a period of 2-2.5 hours. The reaction mixture is warmed to 75° C. and held at this temperature for 2.5 hours. The reaction product is used without further purification.

The viscosity of Example 1 and Reference Example 2 are measured at 100° C. (undiluted):

| Viscosity results | Ex. 1 | Reference Ex. 2 |
|---|---|---|
| D445_100, mm/s$^2$ (cSt) | 29.5 | 146 |

The material of Example 1 is provided, in the amount indicated below, to a test formulation comprising the following additional components:

Synthetic polyalphaolefin oil of lubricating viscosity (to equal 100%)
Polymethacrylate viscosity modifier, 20.4% (including 22% diluent oil)
Polyisobutylene viscosity modifier, 11.5%
Sulfurized olefin antiwear agent(s), 4%
Corrosion inhibitor, 2.5%
Succinimide dispersant 1.25% (including 33% oil)
Commercial antifoam agents, 0.15%
Long chain amine, 0.5%
Material of Example 1: 1.46%

The materials of the present technology provide significantly reduced viscosity compared with the reference material. They also provide good performance in corrosion testing. The materials are also prepared in significantly higher yield or conversion to usefully active components, compared with the reference material.

Each of the documents referred to above is incorporated herein by reference. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration.

What is claimed is:

1. A process for preparing a salt of a hydroxy-substituted ester of phosphoric acid, comprising:
   (a) reacting a phosphate dialkyl diester represented by the formula (RO)$_2$P(=O)—OH, where each R is independently an alkyl group having about 4 to about 30 carbon atoms, with a 1,2-alkylene oxide;
   (b) reacting a product mixture of step (a) with a phosphating agent; and
   (c) reacting a product mixture of step (b) with an amine; wherein the phosphate dialkyl diester is reacted with the alkylene oxide of step (a) in the substantial absence of a phosphate monoester, the amount of said phosphate monoester being 0 to 4 percent by weight of the total phosphate mono- and diester present.

2. The process of claim 1 wherein the amount of phosphate monoester, if any, present in the reaction of step (a) is 0 to 2 percent by weight based on the total amount of phosphate mono- and diester present.

3. The process of claim 1 wherein the R groups comprise 2-ethylhexyl groups.

4. The process of claim 1 wherein the alkylene oxide comprises 1,2-propylene oxide.

5. The process of claim 1 wherein the reaction of step (a) is conducted at about 40 to about 60° C. for about 0.5 to about 4 hours.

6. The process of claim 1, wherein the product mixture prepared by step (a) comprises molecules represented by the formula

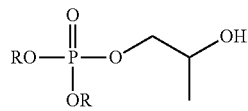

where each R is independently an alkyl group.

7. The process of claim 1 wherein the phosphating agent of step (b) comprises phosphorus pentoxide.

8. The process of claim 1 wherein the product of step (b) comprises a phosphoric ester comprising at least one acid group.

9. The process of claim 1 wherein the product mixture prepared by step (b) comprises molecules represented by the formula

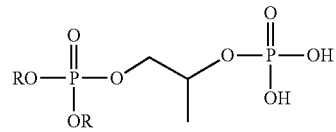

or a mixture thereof with molecules represented by the formula

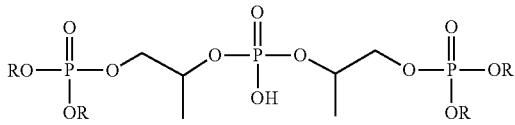

where each R is independently an alkyl group.

10. The process of claim 1 wherein the amine of step (c) comprises at least one secondary amine having about 10 to about 22 carbon atoms.

11. The product prepared by the process of claim 1.

12. A lubricant comprising an oil of lubricating viscosity and the product of claim 11.

13. A method for lubricating a gear, an axle, or a transmission, comprising supplying thereto the lubricant of claim 12.

* * * * *